United States Patent [19]

Tabor et al.

[11] 4,438,098

[45] Mar. 20, 1984

[54] HEAT TREATMENT OF A NON-A, NON-B HEPATITIS AGENT TO PREPARE A VACCINE

[75] Inventors: Edward Tabor, Rockville; Robert J. Gerety, Potomac, both of Md.

[73] Assignee: The United States of America as represented by the Secretary of the Dept of Health & Human Services, Washington, D.C.

[21] Appl. No.: 343,026

[22] Filed: Jan. 27, 1982

[51] Int. Cl.³ ............................................. A61K 39/29
[52] U.S. Cl. ..................................... 424/89; 435/235; 435/236; 435/239
[58] Field of Search .................. 424/89; 435/236, 239, 435/235

[56] References Cited

U.S. PATENT DOCUMENTS 4,291,020  9/1981  Tabor et al. ........................ 424/89

FOREIGN PATENT DOCUMENTS

WO82/00205  1/1982  PCT Int'Appl. ...................... 424/89

OTHER PUBLICATIONS

Tabor et al., Lancet, pp. 463–466, (Mar. 4, 1978).

Tabor et al., Gastroenterology, vol. 76, No. 4, pp. 680–684, (1979).
Tabor et al., The Journal of Infectious Diseases, vol. 140, No. 5, pp. 789–793, (Nov. 1979).
Shih et al., Hepatology, vol. 2, No. 5, p. 681, (1982).
Tabor et al., The Journal of Infectious Diseases, vol. 142, No. 5, pp. 767–770, (Nov. 1980).

Primary Examiner—Thomas G. Wiseman
Assistant Examiner—Frederick W. Pepper
Attorney, Agent, or Firm—John S. Roberts, Jr.

[57] ABSTRACT

A method of treating the agent of human non-A, non-B hepatitis to render it incapable of causing infection which comprises heating said agent at about 60° C. for about 10 hours and recovering the treated protective agent. Furthermore, this treated agent may be utilized as a vaccine, as, for example, inoculating chimpanzees by i.v. inoculation with the heat treated non-A, non-B agent and the animals have been found protected from later challenge by non-A, non-B hepatitis agent. Thus, the second part of the invention resides in the utilization of a heat-treated agent from human plasma later utilized to protect chimpanzees by incoluation and utilization as a vaccine.

2 Claims, 1 Drawing Figure

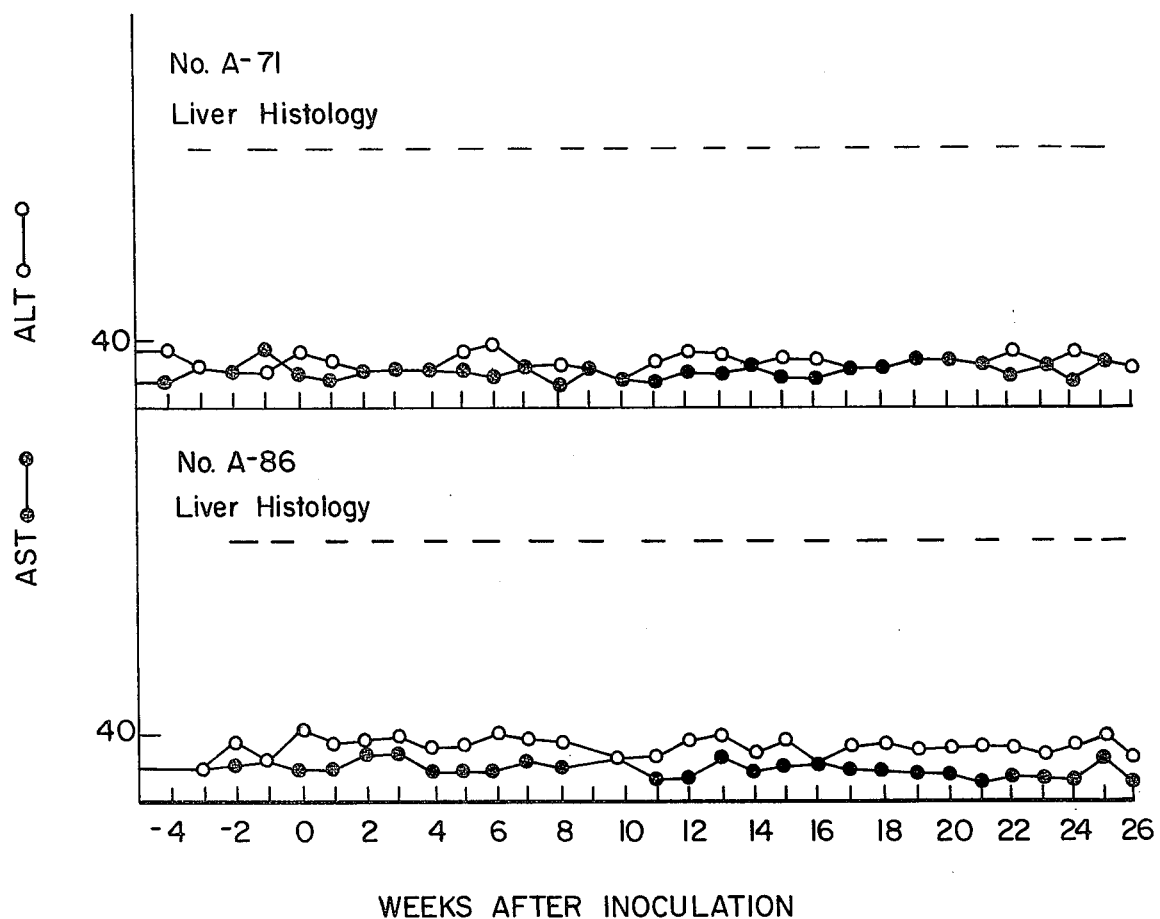

HEAT TREATMENT OF A NON-A, NON-B HEPATITIS AGENT TO PREPARE A VACCINE

This invention relates to a method of inactivating a non-A, non-B hepatitis agent by means of extended heat treatment and this heat treatment is of the optimum value of about 60° C. for 10 hours. About 60° C. was chosen since this value of temperature is about as high as can be tolerated so that the protein will not be inactivated and the antigenicity of the agent will not be affected. Also, the lower limit for inactivating the agent of about 10 hours was selected from positive measure of research as well as kinship to the older and better known HB virus. This heat treatment was utilized so-called "wet" where the agent was in plasma. It is believed that a "dry" process where freeze drying was used would have similar results but the wet process is preferred by the present inventors.

The agent of non-A, non-B hepatitis described here is completely different from the hepatitis A and B viruses. It does not react immunologically with tests for those viruses. Recovery from one agent does not protect against infection by the others.

The present method has utility in that it shows the inactivation of non-A, non-B in animal plasma and further, as a second utilization, may be used in preparation of a vaccine.

The suitability of the chimpanzee as an animal model for the evaluation of this invention has been well documented. Chimpanzees and humans are immunologically and biochemically similar. The chimpanzee has been shown to be susceptible to human non-A, non-B hepatitis and to respond with similar enzyme elevations and similar biopsy changes to those of humans with this infection. See *The Lancet*, Mar. 4, 1978, pp. 463–466, and *The Journal of Infectious Diseases*, Vol. 140, No. 5, Nov. 1979, pp. 789–793.

Non-A, non-B hepatitis has been shown to be caused by a transmissible agent; the chimpanzee has been shown to be a suitable animal model for the study of this disease. The agent of this disease may remain present in blood for prolonged periods of time, but immunity to reinfection has been shown to follow recovery from infection in both humans and chimpanzees.

Statement of prior art

Tabor et al., "Transmission of Non-A, Non-B Hepatitis from Man to Chimpanzee," *Lancet*, Mar. 4, 1978, pp. 463–466.

Tabor et al., "Acute Non-A Non-B Hepatitis Prolonged Presence of the Infectious Agent in the Blood," *Gastroenterology*, Apr. 1979, 76(4) :680-4.

U.S. Pat. No. 4,291,020 Tabor and Gerety. This patent deals with non-A, non-B hepatitis and a vaccine therefrom but is concerned with formalin treatment.

The Drawing

The FIGURE shows aminotransferase levels in liver biopsy specimens obtained at 1-2 week intervals during six months of evaluation.

Example

Plasma from the donor of Inoculum I, obtained in April 1979 was used and was shown to transmit non-A, non-B hepatitis to five of five chimpanzees inoculated intravenously. Samples of this plasma were recalcified; two one ml aliquots of the serum were diluted 1:10 in phosphate buffered saline, pH 7.4, in order to prevent polymerization of albumin in the serum during heating. Starting materials containing less albumin or inhibitors of polymerization would not require dilution. Each sample was heated at 60° C. for about 10 hours while monitoring the temperature in a control vial at 20 minute intervals. Each sample was then inoculated intravenously into one of two colony-born infant chimpanzees with no prior exposure to blood or plasma derivatives. Aminotransferase levels remained within normal limits in weekly serum samples, and no evidence of hepatitis was detected in liver biopsy specimens obtained at one- to two-week intervals during six months of evaluation (see FIGURE ). Subsequent inoculation of these two chimpanzees with unheated samples of Inoculum I demonstrated that the inactivated material had induced immunity to non-A, non-B hepatitis. One of the two chimpanzees was completely protected and had no aminotransferase elevations or liver biopsy abnormalities. The other was partially protected and had only a modified infection after the challenge inoculation.

Non-A, non-B hepatitis has been shown to be caused by a transmissible agent; the chimpanzee has been shown to be a suitable animal model for the study of this disease. The agent of this disease may remain present in blood for prolonged periods of time, but immunity to reinfection has been shown to follow recovery from infection in both humans and chimpanzees.

We claim:

1. A method of treating the agent of human non-A, non-B hepatitis to render it incapable of causing infection which consists essentially of heating said agent contained in serum or plasma at about 60° C. for about 10 hours and recovering said treated agent.

2. A method of producing a vaccine which comprises inoculating chimpanzees with an agent prepared according to claim 1 and thereby protecting from later challenge by a non-A, non-B hepatitis agent and workup and recovery of antibodies to said vaccine.

* * * * *